US00PP09225P

United States Patent [19]

Ison

[11] Patent Number: Plant 9,225

[45] Date of Patent: Aug. 1, 1995

[54] MUSCADINE GRAPE 'EARLY FRY'

[76] Inventor: William G. Ison, 3801 Johnson Dr., Lithonia, Ga. 30058

[21] Appl. No.: 241,750

[22] Filed: May 12, 1994

[51] Int. Cl.[6] ..... A01H 5/00
[52] U.S. Cl. ..... Plt./47.2
[58] Field of Search ..... Plt. 47.2

[56] References Cited

U.S. PATENT DOCUMENTS

P.P. 7,265 7/1990 Ison ..... Plt./47.2

*Primary Examiner*—James R. Feyrer
*Attorney, Agent, or Firm*—James A. Hinkle

[57] ABSTRACT

A cross between the female variety Sweet Jenny and the pollen parent variety Ison to produce an improved variety of muscadine grape.

1 Drawing Sheet

DESCRIPTION OF THE VARIETY

A cross between Ison and Sweet Jenny.

The primary objective of the breeding was to produce an improved variety of muscadine plant that has fruit which ripens early so as to extend the season of muscadine production. The fruit is large, sweet, bronze, dry scar for longer shelf life, female, and has characteristics that are superior to either of its parents. These characteristics include the plant having even ripening fruit with high acid, and the plant being vigorous and productive.

In comparision with both the seed and pollen parent, the new variety is not similar in color to the pollen parent which is black. The new variety has the characteristics of earliness which is also characteristics of the pollen parent, and has the size and color of the seed parent. The fruit of this new variety is more dry scar with clusters ripening approximately 100% uniformly. The present variety yields on the average of five to eight tons per acre in tests conducted at Ison's Nursery & Vineyards, Brooks, Ga. The fruit from this plant has an excellent flavor.

Asexual reproduction of the new variety either by soft wood cuttings or by layering as performed at Brooks, Ga., shows that the foregoing characteristics and distinctions come true to form and are established and transmitted through succeeding propagations.

The accompanying photograph shows a typical specimen of the vegetative growth and fruit of the new variety when the fruit is ripe and ready for picking. The photograph depicts the variety in color as truly as it is reasonably possible to make the same in a color illustration.

The following is a detailed description of the new variety:

Species: *Vitis rotundifolia.*
Type: Vine.
Seep parent: Sweet Jenny.

Pollen Parent: Ison.
Propagation: Holds its characteristics through succeeding propagation by either layering or by soft wood cuttings.
Locality where grown: Brooks, Ga.
Fruit:
- *Borne.*—Usually in clusters of five to fifteen berries. This new variety ripens one to two weeks earlier than the pollen parent, Ison.
- Size.—Up to $1\frac{1}{4}''$ diameter, similar in size to seed parent (Sweet Jenny); almost 100% even ripening.
- *Color.*—Greyed Orange, 165C Fan 4 Royal Horticultural Society, London, England.
- *Sugar content.*—18.5% to 21% soluble solids average.
- *Shape.*—Round.
- *Seed.*—Average diameter $\frac{1}{8}1''$ average seed per berry 2.65.
- *Pulp.*—Color: Greyed Green, 194C, Royal Horticultural Society, Fan 4, London, England. Consistency: Medium soft and juicy as compared to most muscadine vines.
- *Skin.*—Medium thick.

Foliage: Leaf color Green Group 136B Fan 3 Royal Horticultural Society, London, England. Leaf size and shape similar to most muscadine varieties.
Reproductive organs: Female.
Growth habits: Requires support, very productive and vigorous, dry scar, disease resistant, early season.
Canes: Medium.
Diseases: Tolerant to Muscadine diseases.

This description was made from a muscadine vine grown at Ison's Nursery & Vineyards, Brooks, Ga.

I claim:

1. The new and distinct variety of grape plant as described and illustrated.

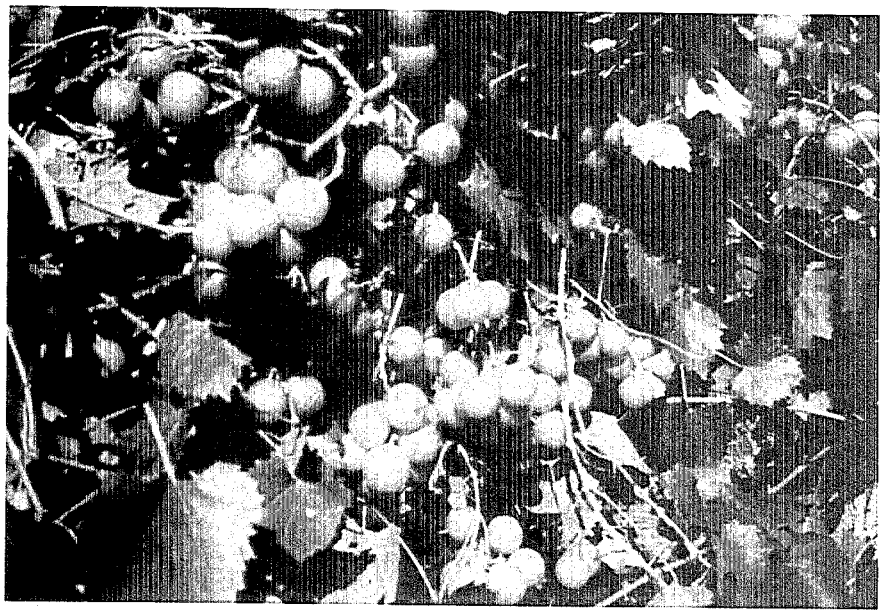

* * * * *